United States Patent [19]

Laauwe

[11] Patent Number: 4,596,157
[45] Date of Patent: Jun. 24, 1986

[54] DEVICE FOR OBTAINING, TRANSPORTING AND USING A LIQUID SPECIMEN

[76] Inventor: Robert H. Laauwe, 237 Green Ridge Rd., Franklin Lakes, N.J. 07417

[21] Appl. No.: 751,324
[22] Filed: Jul. 2, 1985
[51] Int. Cl.$^4$ ............................................. G01N 1/12
[52] U.S. Cl. ................................ 73/864.72; 128/767
[58] Field of Search ........... 73/864.72, 864.01, 864.11, 73/864.16; 128/759, 761, 763, 765, 767

[56] References Cited

U.S. PATENT DOCUMENTS 2,847,000   8/1958   Nieburgs ............................ 128/759
3,966,558   6/1976   Pellicer .............................. 128/759

Primary Examiner—Jerry W. Myracle
Attorney, Agent, or Firm—Kenyon & Kenyon

[57] ABSTRACT

A device for obtaining, transporting and dispensing a liquid specimen, has a tubular handle having a front portion and front and back ends, a body of liquid absorbent material positioned slidably in the front portion of the handle, and a rod having an end connected to the body and extending through the handle to and through the back end of the handle and having an actuating portion projecting from the back end of the handle for sliding the body forwardly to a projected position where the body is exposed beyond the front end of the handle for contact and absorption by the liquid specimen, and backwardly to a retracted position where the body is returned within the front end portion of the handle and radially enclosed by the handle for transporting the specimen, the body having substantially the same external transverse shape and dimensions as the inside transverse shape and dimensions of the front position of the handle and being substantially free from compression when slid to said retracted position, and the handle having a wall with which the body radially registers when at the retracted position and which wall is radially inwardly flexible under external pressure to radially compress the body and squeeze at least some of the absorbed liquid from the body and dispensing the specimen through the front end of the handle.

7 Claims, 8 Drawing Figures

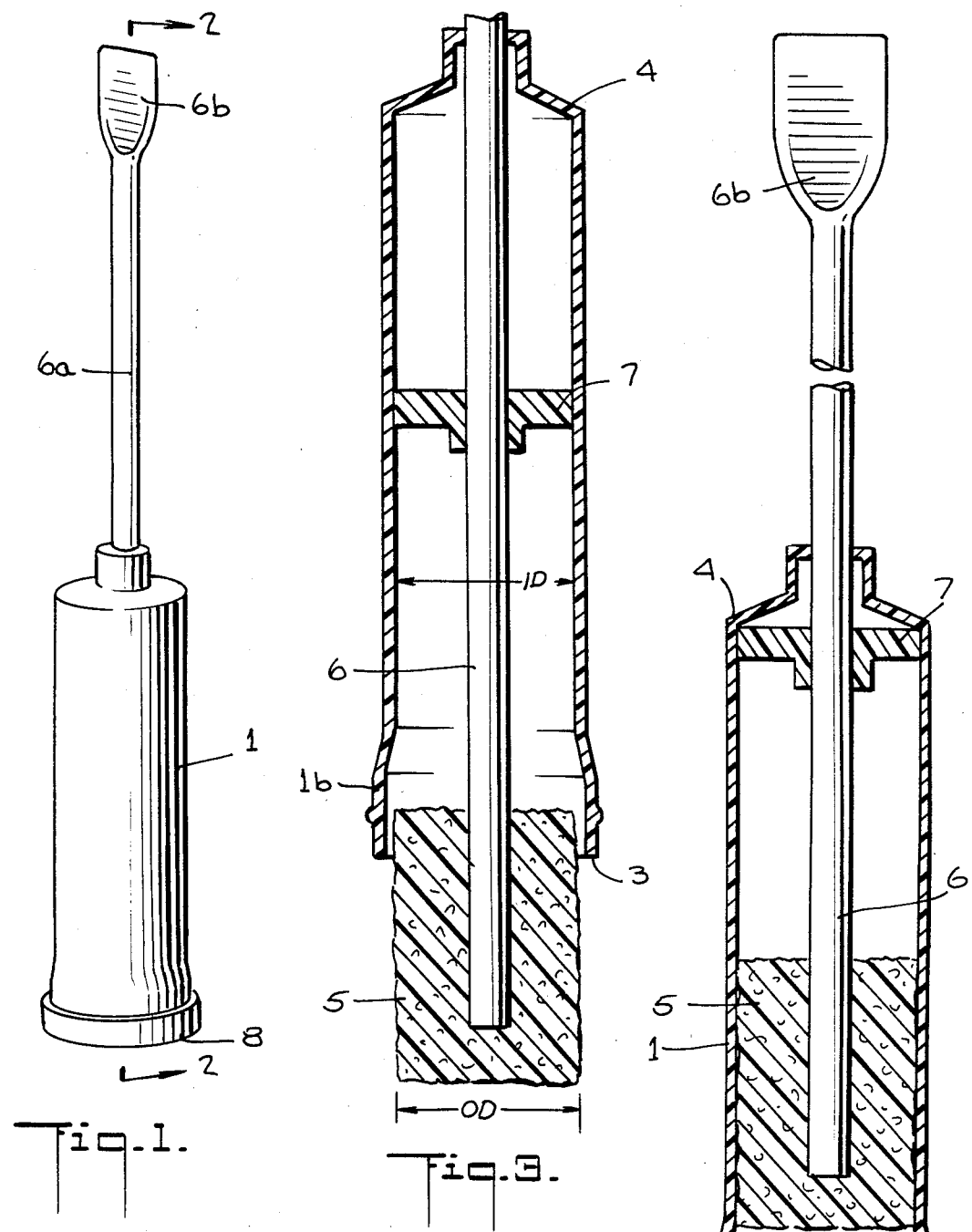
Fig. 1.
Fig. 3.
Fig. 2.
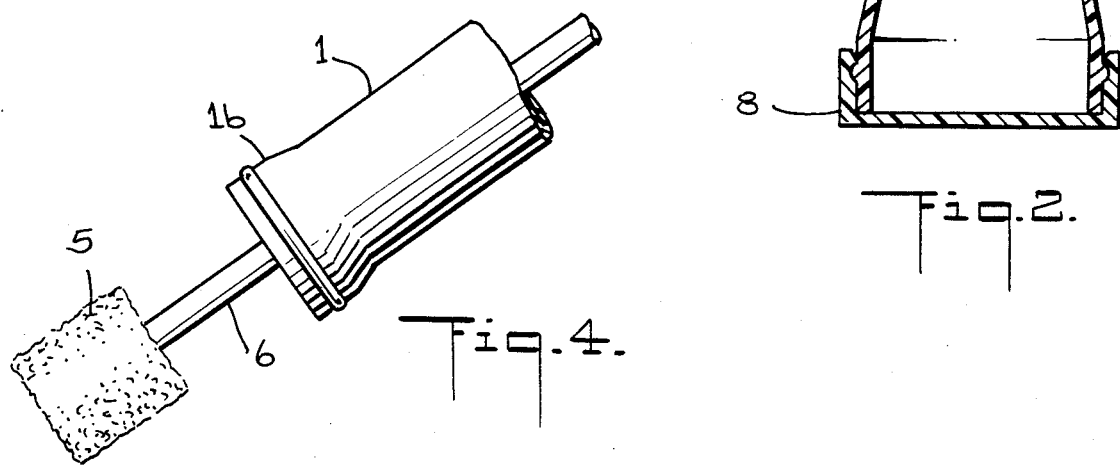
Fig. 4.

DEVICE FOR OBTAINING, TRANSPORTING AND USING A LIQUID SPECIMEN

FIELD OF THE INVENTION

This invention relates to the field of devices for obtaining, transporting and using a liquid specimen, particularly a specimen of urine as is often required by physicians and by persons using one of the currently available home medical kits of the type requiring drops of urine to be dropped on a sensitized surface for the detection of diabetes, pregnancy and other conditions.

BACKGROUND OF THE INVENTION

Heretofore when a specimen of urine is required it has been customary to deposit the urine in a container such as a beaker in a physician's office for direct analysis, or in the home by using any convenient container such as a used and washed jelly glass. For men this has been a simple procedure but for women it has been difficult, frequently involving wetting of the hands holding the container and in general presenting an unpleasant situation. These problems are particularly acute when a specimen partially through urination is required.

In an attempt to provide a better way to obtain a specimen, U.S. Pat. No. 4,014,322 proposes the use of a liquid absorbent body on a handle, which is placed in the stream of urine and then transferred into a container where it is squeezed so that a liquid specimen is delivered into the container. A relatively large specimen is obtained.

However, normally the physician or a user of one of the home medical test kits requires only a few drops of specimen. In the usual case or when the above mentioned patented arrangement is used, the container with an excess of urine specimen is sampled by the use of a medicine dropper or its equivalent, so as to provide the one or a few drops of specimen required.

In some cases where the specimen must be dropped on a sensitized surface it is necessary to rub the specimen on the surface. The home type of kit has been provided with a medicine dropper having an end forming what is in effect a spatula which is used for this purpose.

The object of the present invention is to provide a device for collecting, transporting and using a specimen of urine, in a manner that is more convenient, more secure and less unpleasant. The transporting may be either in a person's home from the point of collection of the specimen to a home medical test kit, or for collecting at home and transporting the specimen to a physician's office.

GENERAL DESCRIPTION OF THE INVENTION

According to the present invention a tubular handle has a front portion and front and back ends. This handle portion may comprise a relatively short length of elastically flexible plastic tube of any convenient cross sectional shape. A body of liquid absorbent material is positioned slidably in the front portion of the handle and a rod having an end connects to the body and extends through the handle to and through the back end of the handle for sliding the body forwardly to a projected position where the body is exposed beyond the front end of the handle for contact and absorption by the liquid specimen. For example, by using the handle the exposed absorbent material body can be placed in a stream of urine without wetting of the hands.

After the body of absorbent material has absorbed some of the specimen, the actuating portion of the rod is used for sliding the body containing the absorbed specimen, to a retracted position where the body is retained within the front end of the handle and radially enclosed by the handle for transporting the specimen. Transporting without leakage is possible because the body is made with substantially the same external dimensions and shape as the inside shape and dimensions of the handle so that the body is substantially free from compression when slid to its retracted position inside of and protected by the handle. The handle has at least one wall portion with which the body radially registers when at its retracted position and which wall is radially inwardly flexible under external pressure to radially compress the body and squeeze the absorbed liquid from the body so as to deliver the specimen as drops, through the front end of the handle.

The absorbent material from which the specimen collecting body is formed should be such that after absorbing the liquid the body is substantially dripless and when at its retracted position within the handle retains the absorbed liquid against gravitational loss until squeezed from the body. This permits the device to be carried safely to the physician's office or about the home to a home testing kit. Normally such a kit requires a certain number of drops of the urine specimen to be deposited onto the reactive elements of the kit, and by squeezing the handle judiciously one drop after another can be delivered where required. No separate medicine dropper is required.

Preferably the handle is formed by a short length of plastic tube that is elastically deformable radially inwardly throughout its length and which resists inward deformation during normal transportation of the device but elastically deforms inwardly under firm external pressure deliberately applied to squeeze the absorbed liquid from the body inside of the tube.

Means are provided for guiding the rod substantially concentrically with the inside of the tube. For example, this can be in the form of a washer having a hole through which the rod is fixed, or slidably extends, and having an exterior periphery which slidably fits the inside of the tube. Although the plastic tube forming the handle of the device can be a simple straight length of plastic tube, the front end of the tube can be slightly flared so as to guide the body with its absorbed specimen, into the front portion of the tube during movement of the body from its projected position backwardly to its retracted position inside of the tube.

The outer end of the actuating rod can be formed as a spatula to assist in spreading or smearing the drops of dispensed specimen on the reactive material of a home medical kit when required by the kit's instructions.

Finally, the front end of the tube can be provided with a removable closure such as an end cap with a friction fit or a ring snap lock holding the cap on until removed for using the specimen.

DESCRIPTION OF THE DRAWINGS

The presently preferred form of this new device is illustrated by the accompanying drawings in which:

FIG. 1 is a perspective view of the device;

FIG. 2 is a vertical section of the device;

FIG. 3 is similar to FIG. 2 but shows the absorbent body being pushed or slid to its extended position;

FIG. 4 is a perspective view showing the device with the absorbent body extended for use;

FIG. 5 is a vertical section like FIG. 3 but showing the use of a tube without the flared end or cap previously referred to;

DETAILED DESCRIPTION OF THE INVENTION

Figure 5:
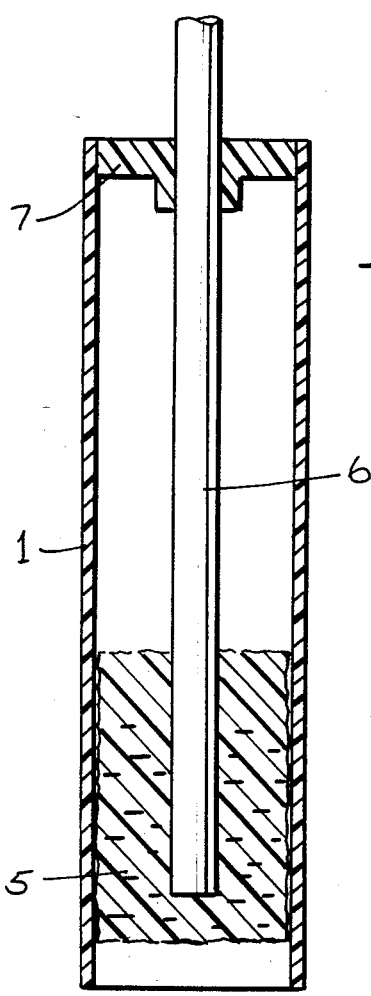

In the above drawings, the tubular handle 1 has the front portion 2 and front and back ends 3 and 4 respectively. The body of liquid absorbent material 5 is positioned slidably in the front portion 2 of the handle, and a rod 6 has an end connected to the body 5 and extending through the handle to and through the back end of the handle with an actuating portion 6a projecting from the back end 4 of the handle for sliding the body 5 forwardly to a projected position where the body is exposed beyond the front end of the handle, as shown by FIG. 4, for contact and absorption by the specimen. After absorption the body 5 can be pulled backwardly by the actuating portion 6a of the rod 6 to a retracted position where the body is retained within the front end portion of the handle and radially enclosed by the handle for transporting the specimen, as shown by FIG. 2.

Assuming the tubular body and absorbent body 5 are of circular cross section the outside diameter OD of the body and the inside diameter ID of the tubular handle are substantially the same so that the body 5 is slidable within the tubular hands and is substantially free from compression when slid to its retracted position as shown by FIG. 2. At least the wall portion of the handle which radially registers with the body when the body is at its retracted position, is radially inwardly flexible under external pressure to radially compress the body and squeeze at least some of the absorbed liquid from the body so as to deliver the specimen through the front end of the handle. This action is illustrated by FIGS. 6 and 7.

The cross-sectional shape of the tubular handle can be circular, oval or other convenient shape. An oval shape has the advantage that when held with its narrow side down, the formation of drops is facilitated.

Figure 6:
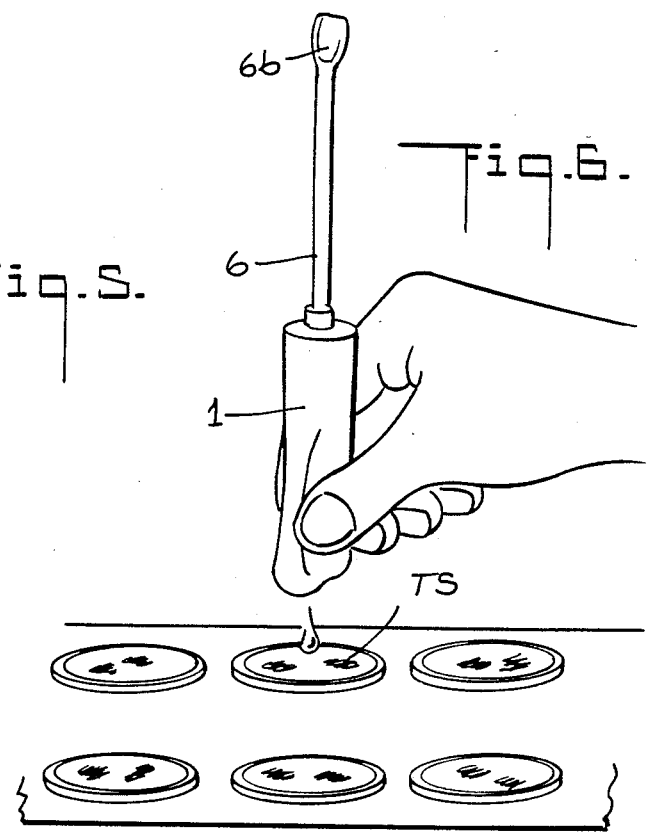
FIG. 6 is a perspective view showing the device in use dispensing the absorbed specimen one drop at a time on a sensitized surface of a home medical kit.
Figure 7:
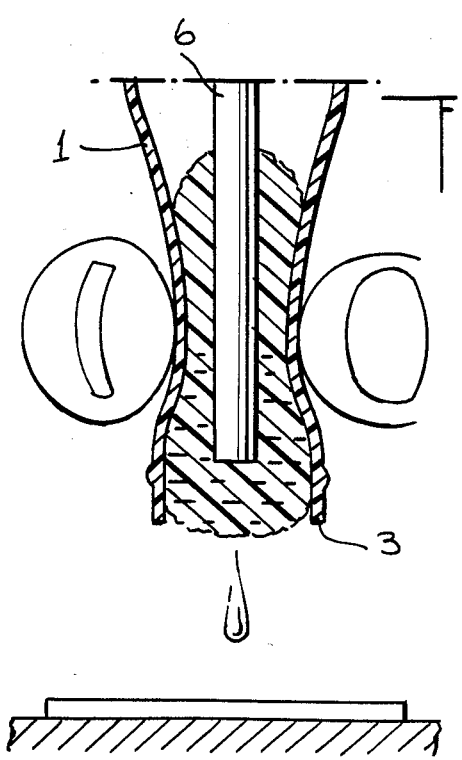
FIG. 7 in vertical cross section shows how the absorbent material body can be compressed by externally applied finger pressure.

When the kit used is of the type providing a card having a pregnancy rapid spot test surface, as shown by FIG. 6, the new device is used to squeeze the required number of drops of urine specimen onto a test spot TS of the kit. A typical kit encloses a medicine dropper which is dipped into a specimen in an open container in which the specimen was deposited, and which is then dropped onto the test spot of the kit according to the instructions of the manufacturer of the kit. The medicine dropper used has been provided with an end forming a spatula, used to mix the deposited specimen on the test spot TS.

Figure 8:
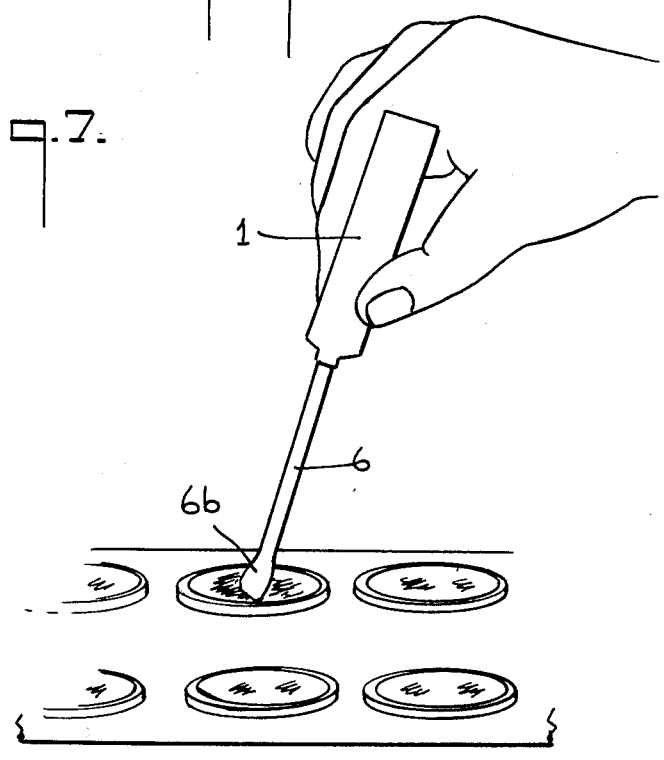
FIG. 8 in perspective shows how the end of the actuating rod can be formed as a spatula and used to distribute the specimen over the reactive surface of a kit.

With the present invention the outermost end of this actuating portion 6a of the rod 6 is formed as a spatula 6b and as shown in FIG. 8, this spatula can be used to mix the specimen with the test spot.

The tubular handle 1 is preferably formed by a short length of elastically flexible plastic tube that is elastically deformable radially inwardly throughout its length. It should resist inward deformation during normal handling and transportation of the device, but be elastically deformed inwardly under firm external pressure applied to squeeze the absorbed specimen from the body. In other words the tube should be elastically deformable inwardly under intentionally applied firm finger pressure on the outside of the tube, but it should not be so elastically deformable or soft or limber that normal handling causes squeezing of the specimen-containing body inside of the tube.

The device has means for guiding the rod 6 concentrically with the inside of the tube. This takes the form of a disc 7 having an outside diameter slidably fitting the inside of the tube, the disc 7 being preferably fixed to the rod 6. The disc 7 can be spaced so that when the body is in its retracted position as shown by FIG. 2 the disc is positioned just at the outermost or back end of the tube 1. At this back end the tube has a frusto-conical end, the rod 6 extending through that end, but the back end can be formed only by a straight cut through to the tube used as in FIG. 5.

The front end of the tube forming the handle can be slightly flared at 1b so as to guide the body into the front portion of the tube during retraction of the body from its projected position backwardly to its retracted position. However, because the outer dimensions and shape of the body are substantially the same as the inner dimensions and shape of the tube satisfactory operation is obtained when the tube is made with the same dimensions and shape throughout its extire extent as shown by FIG. 5.

The front end of the handle or tube 1 can be provided with a removable closure or cap 8 which can be frictionally held on that end or provided with a ring lock as indicated in FIG. 2.

The device of this invention can be made entirely of plastic excepting that the absorbent body 5 should be a plastic foam, or other material, having adequate absorption and liquid retaining characteristics. The device is inexpensive and the devices can be included as part of a home medical test kit which normally consists of a card having sensitized portions and medicine droppers possibly having ends forming a spatula. When part of such a kit, the operation of the device is shown by FIGS. 6 through 8. FIG. 4 shows how the absorbent body can be extended entirely free from the handle 1 and placed in a stream of urine, after which, using the rod's actuating portion 6a, the body is withdrawn to the position shown by both FIGS. 2 and 5. When in this position the device can be transported for either short or longer distances without leakage. When indicated the cap 1b can be applied for protection against possible contamination of the specimen. It is not necessarily required to prevent leakage. The device can be safely carried to a physician's office in a ladies handbag or shipped in a rigid mailing tube. At home the device can be easily and safely carried from the bathroom to a home medical testing kit. At the kit, as previously described, finger pressure applied as shown by FIG. 7 can cause the specimen to be delivered one drop at a time on the testing spot of the card provided customarily with such a kit, and afterwards the specimen can be distributed on the test spot by using the spatula on on the rod's actuating portion 6a.

Particularly in the case of women the device can be used fastidiously, unobtrusively and without hand wetting. Of greater importance is the fact that after absorbing the specimen the body can be pulled back into its retracted position without loss of the urine specimen, the device then becomes a container substantially completely enclosing and protecting the specimen. No eye dropper is required, controlled squeezing of the tubular handle formed by the elastically flexible plastic tube permitting one drop, or a specified number of drops, to be cleanly and neatly deposited on a test spot of the kit.

Home kits are normally furnished with a number of eye droppers, or the equivalent, which are each discarded after each use. Because of the inexpensiveness of the device of this invention, the same number of devices can be provided a home test kit, excepting that each device is self-contained.

This new device can be made very inexpensively by the use of the commercially available extruded plastic tube which can be obtained in any length desired. By cutting this tube to appropriate lengths the handles for the devices can be provided, each cut length having straight-cut opposite ends. The use of injection molding with its attendant expense is made unnecessary by this practice. The plastic tube used can be extruded from low-density polyethylene or other extruded tube of plastic having the physical properties previously indicated. To prevent inadvertent excessive withdrawal of the rod 6 through the back end of such a simplified construction, that end of the tube can be inexpensively thermally shaped to provide a stop for the washer.

Physicians making a complete urine analysis may require a somewhat larger specimen, such as in the area of a fraction of an ounce, and in such instances it is only necessary to make the device on a larger scale than would normally be used when provided as part of a home analysis kit. For example, for home medical kit use the device may have an overall diameter in the area of from 0.25 to 0.30 of an inch, and a length of only 2 to 3 inches, or approximations of such dimensions.

What is claimed is:

1. A device for obtaining, transporting and dispensing a liquid specimen, comprising a tubular handle having a front portion and front and back ends, a body of liquid absorbent material positioned slidably in the front portion of the handle, and a rod having an end connected to the body and extending through the handle to and through the back end of the handle and having an actuating portion projecting from the back end of the handle for sliding the body forwardly to a projected position where the body is exposed beyond the front end of the handle for contact and absorption by the liquid specimen, and backwardly to a retracted position where the body is returned within the front end portion of the handle and radially enclosed by the handle for transporting the specimen, said body having substantially the same external transverse shape and dimensions as the inside transverse shape and dimensions of the front position of the handle and being substantially free from compression when slid to said retracted position, and the handle having a wall with which the body radially registers when at said retracted position and which wall is radially inwardly flexible under external pressure to radially compress the body and squeeze at least some of the absorbed liquid from the body and dispensing the specimen through the front end of the handle.

2. The device of claim 1 in which the absorbent material after absorbing the liquid is substantially dripless and when the body is at the retracted position retains substantially all of the absorbed liquid against gravitational loss until squeezed from the body.

3. The device of claim 2 in which said handle is formed by a plastic tube that is elastically deformable radially inwardly throughout its length and which resists inward deformation during normal transportation of the device but elastically deforms inwardly under firm external pressure applied to squeeze the absorbed liquid from the body.

4. The device of claim 3 in which within the tube the rod has means for guiding it substantially concentrically with the inside of the tube.

5. The device of claim 4 in which the front end of the tube is slightly flared and guides the body into the front portion of the tube during movement of the body from its projected position backwardly to its retracted position.

6. The device of claim 4 in which the rod has an outer end forming a spatula.

7. The device of claim 4 in which the front end of the tube is provided with a removable closure.

* * * * *